(12) United States Patent
Vazquez et al.

(10) Patent No.: US 8,479,595 B2
(45) Date of Patent: Jul. 9, 2013

(54) SENSOR ASSEMBLY AND MEDICAL DEVICE INCORPORATING SAME

(75) Inventors: Pablo Vazquez, Granada Hills, CA (US); Hsiao-Yu S. Kow, Ladera Ranch, CA (US); Afshin Bazargan, Simi Valley, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 318 days.

(21) Appl. No.: 12/908,809

(22) Filed: Oct. 20, 2010

(65) Prior Publication Data

US 2012/0096954 A1 Apr. 26, 2012

(51) Int. Cl.
*G01D 1/00* (2006.01)

(52) U.S. Cl.
USPC .................................. 73/862.53; 73/862.627

(58) Field of Classification Search
USPC .................. 73/760, 862.53, 862.627
See application file for complete search history.

(56) References Cited

U.S. PATENT DOCUMENTS

| | | | |
|---|---|---|---|
| 3,631,847 A | 1/1972 | Hobbs, II | |
| 3,970,982 A * | 7/1976 | Kurtz et al. | 338/4 |
| 4,212,738 A | 7/1980 | Henne | |
| 4,270,532 A | 6/1981 | Franetzki et al. | |
| 4,282,872 A | 8/1981 | Franetzki et al. | |
| 4,362,218 A * | 12/1982 | Shoberg | 177/154 |
| 4,373,527 A | 2/1983 | Fischell | |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,494,950 A | 1/1985 | Fischell | |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic Minimed, Inc.

(Continued)

*Primary Examiner* — Max Noori
(74) *Attorney, Agent, or Firm* — Ingrassia Fisher & Lorenz, P.C.

(57) ABSTRACT

Apparatus are provided for sensor assemblies and related medical devices. An embodiment of a sensor assembly includes a beam and a sensing element disposed on the beam. The sensor assembly also includes a loading member to deflect the beam in response to a force applied to the sensor assembly. The loading member has a feature that prevents deflection of the beam when the force applied is greater than a threshold value.

23 Claims, 10 Drawing Sheets

U.S. PATENT DOCUMENTS

| | | | |
|---|---|---|---|
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,113,709 A * | 5/1992 | Ekola | 73/862.638 |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,319,980 A | 6/1994 | Kremidas | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,438,883 A * | 8/1995 | McLean | 73/862.632 |
| 5,482,473 A | 1/1996 | Lord et al. | |
| 5,485,408 A | 1/1996 | Blomquist | |
| 5,497,772 A | 3/1996 | Schulman et al. | |
| 5,505,709 A | 4/1996 | Funderburk et al. | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Iliff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach | |
| 5,868,669 A | 2/1999 | Iliff | |
| 5,871,465 A | 2/1999 | Vasko | |
| 5,879,163 A | 3/1999 | Brown et al. | |
| 5,879,360 A | 3/1999 | Crankshaw | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,248,093 B1 | 6/2001 | Moberg | |
| 6,259,937 B1 | 7/2001 | Schulman et al. | |
| 6,329,161 B1 | 12/2001 | Heller et al. | |
| 6,368,314 B1 | 4/2002 | Kipfer et al. | |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,485,465 B2 | 11/2002 | Moberg et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |

| | | |
|---|---|---|
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0010789 A1 | 1/2007 | Peter et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO95/20145 | 7/1995 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO2004/052429 A1 | 6/2004 |
| WO | WO 2005/065538 A2 | 7/2005 |
| WO | WO2008/001881 A1 | 1/2008 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-Tron® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.

(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.

Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

Search Report for PCT/US2011/05988, Feb. 3, 2012, Medtronic Minimed, Inc.

* cited by examiner

SENSOR ASSEMBLY AND MEDICAL DEVICE INCORPORATING SAME

CROSS-REFERENCE TO RELATED APPLICATIONS

The subject matter described here is related to the subject matter described in U.S. patent application Ser. No. 12/908,807, and U.S. patent application Ser. No. 12/908,812, both filed concurrently herewith.

TECHNICAL FIELD

Embodiments of the subject matter described herein relate generally to sensors and medical devices that utilize sensors. More particularly, embodiments of the subject matter relate to sensor assemblies configured to limit deflection of a beam having a sensing element disposed thereon.

BACKGROUND

Force sensors can be found in electronic devices and may be utilized for various applications. For example, infusion pump devices and systems are relatively well-known in the medical arts, for use in delivering or dispensing an agent, such as insulin or another prescribed medication, to a patient. Some infusion pump devices utilize a force sensor to detect an occlusion in a fluid path when administering the agent.

A typical infusion pump includes a pump drive system which typically includes a small motor and drive train components that convert rotational motor motion to a translational displacement of a stopper (or plunger) in a reservoir. The reservoir cooperates with tubing, a catheter and/or an infusion set to create a fluid path for carrying medication from the reservoir to the body of a user. Some fluid infusion devices include an occlusion detection feature that determines when an occlusion develops in the fluid path. Thus, medication infusion pump devices have included force sensors designed to detect and indicate a pump malfunction and/or non-delivery of the medication to the patient due to a fluid path occlusion. However, relatively small force sensors that provide relatively high sensitivity and/or accuracy over a narrow range of values (which may be necessary for occlusion detection) may be more susceptible to damage as a result of a physical impact or an applied force exceeding the intended measurement range.

BRIEF SUMMARY

An embodiment of a sensor assembly is provided. The sensor assembly includes a beam and a sensing element disposed on the beam. The sensor assembly also includes a loading member to deflect the beam in response to a force applied to the sensor assembly. The loading member has a feature that prevents deflection of the beam when the force applied is greater than a threshold value.

Also provided is an embodiment of a portable medical device. The portable medical device includes a sliding member and a drive system to displace the sliding member in a first direction. A sensor assembly is coupled to the drive system to measure force provided by the drive system to displace the sliding member in the first direction. The sensor assembly comprises a beam, a sensing element disposed on the beam, and a loading member. The loading member deflects the beam in response to a force applied to the sensor assembly and inhibits deflection of the beam when the force applied to the sensor assembly is greater than a threshold value.

Another embodiment of a sensor assembly is also provided. This embodiment of the sensor assembly comprises a beam structure and a loading element. The beam structure comprises a plurality of beams extending from an outer portion, wherein end portions of the beams are integral to provide an inner portion of the beam structure. Each beam has a sensing element disposed thereon. The loading element is mechanically coupled to the inner portion to deflect one or more of the plurality of beams in response to a force applied to the loading element. The loading element contacts the outer portion to restrict displacement of the inner portion when the force applied is greater than a threshold value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
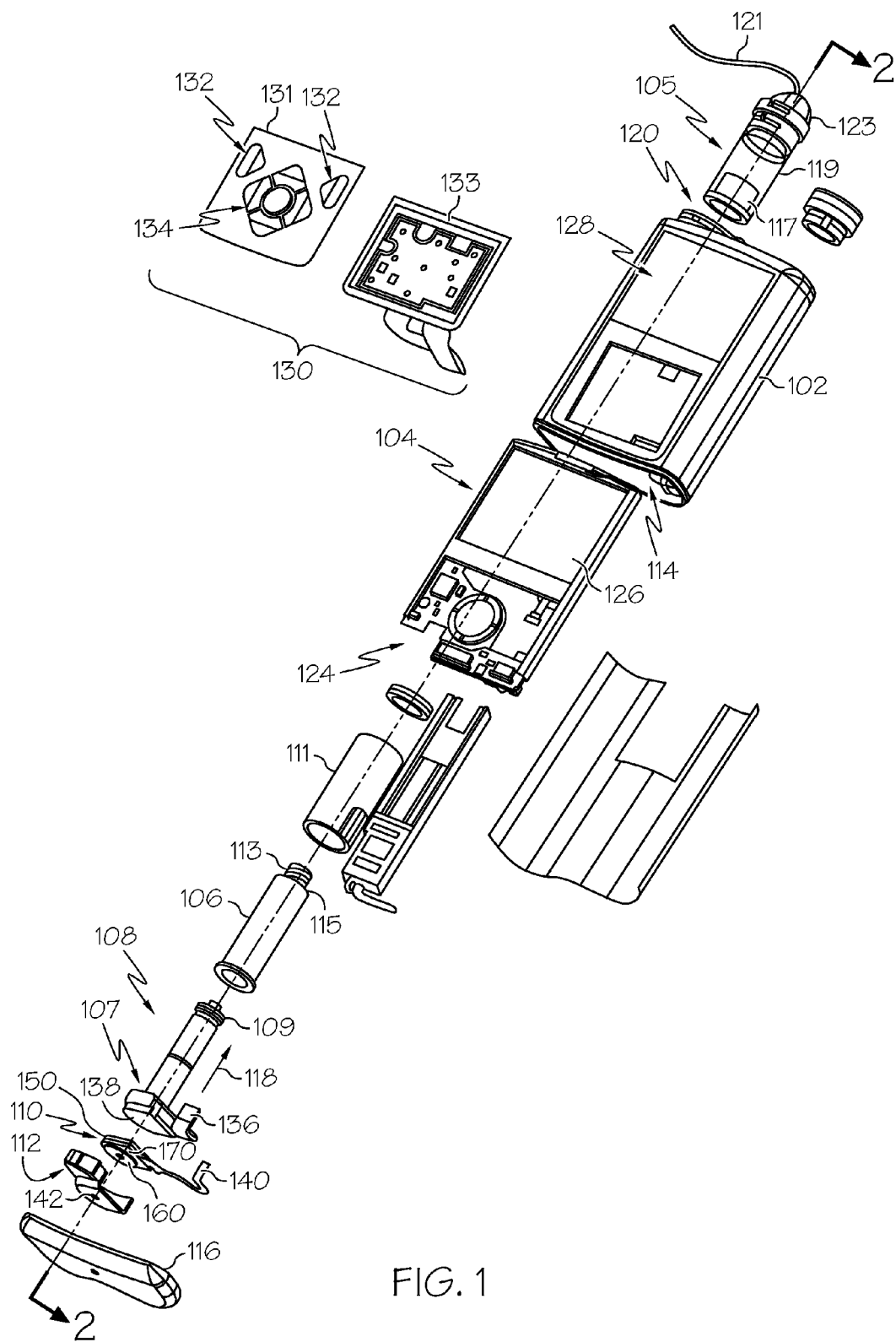
FIG. 1 is an exploded perspective view of an exemplary embodiment of an infusion pump.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The following description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the following description for the purpose of reference only, and thus are not intended to be limiting. For example, terms such as "upper", "lower", "above", and "below" might refer to directions in the drawings to which reference is made. Such terminology may include the words specifically mentioned above, derivatives thereof, and words of similar import. Similarly, the terms "first", "second", and other such numerical terms referring to structures do not imply a sequence or order unless clearly indicated by the context.

The technologies described below can be implemented in any electronic device having one or more sensors incorporated therein. Although the subject matter is applicable to any electronic device where it may be desirable to utilize the sensor assemblies described herein, the exemplary embodiments are implemented in the form of medical devices, such as portable electronic medical devices. Although many different applications are possible, the following description focuses on an infusion pump as part of an infusion system deployment. For the sake of brevity, conventional techniques related to infusion system operation, insulin pump and/or infusion set operation, force sensor design and operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893 which are herein incorporated by reference.

Figure 2:
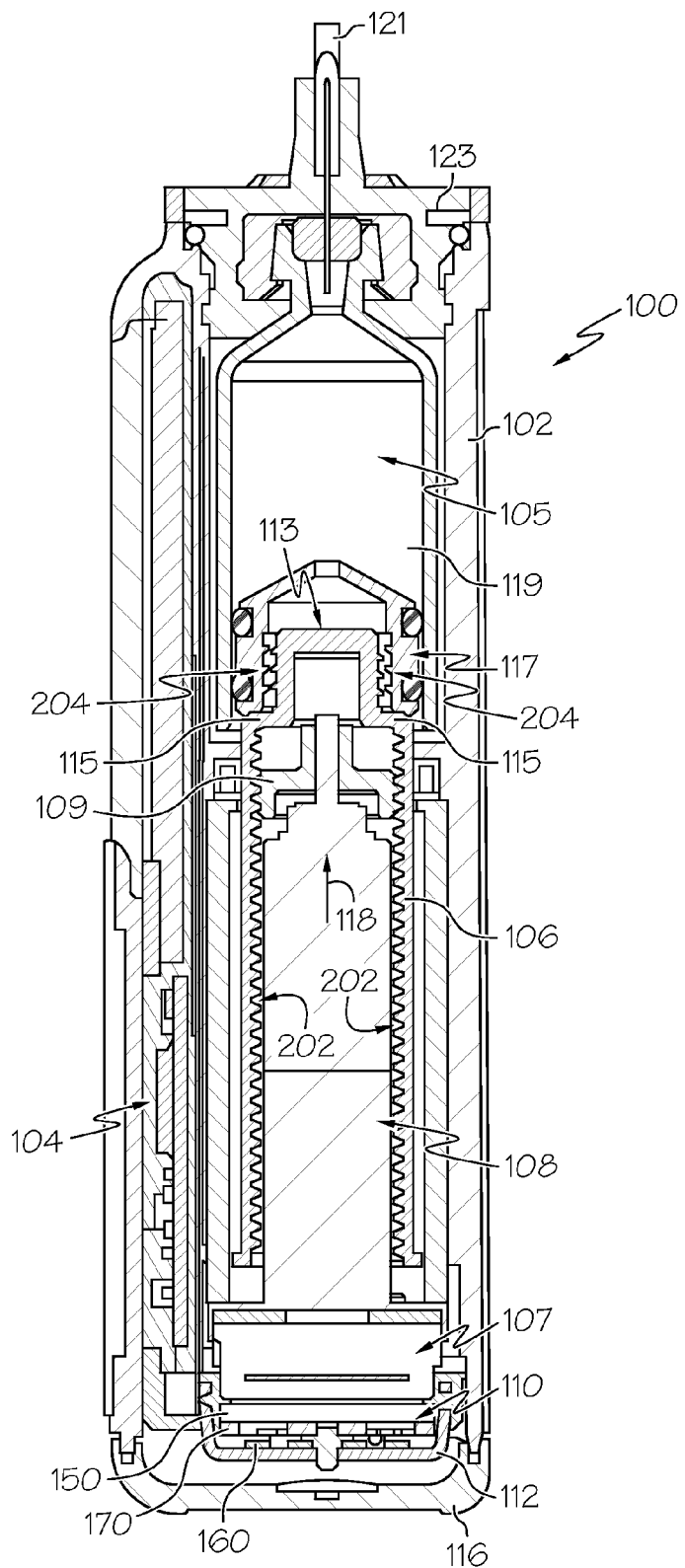
FIG. 2 is a cross-sectional view of the infusion pump as viewed along line 2-2 in FIG. 1 when assembled with a reservoir inserted in the infusion pump of FIG. 1.

FIGS. 1-2 depict an exemplary embodiment of an infusion pump 100. The infusion pump 100 is designed as a portable medical device suitable for infusing fluid into the body of a user, and in practice, may be carried or worn by the user. The infusion pump 100 may be configured to be interoperable with an infusion set as part of an insulin infusion system. The components of an insulin infusion system may be realized using different platforms, designs, and configurations, and the embodiment shown in FIG. 1 is not exhaustive or limiting. Moreover, as mentioned previously, other devices in an infusion system, other medical devices designed to address other patient needs, and other portable electronic devices could utilize a sensor assembly having the characteristics described herein.

The illustrated embodiment of infusion pump 100 includes, without limitation, a housing 102, an electronics assembly 104, a sliding member (or slide) 106, a drive system 108, a sensor assembly 110, and a capping member 112. The housing 102 includes an opening 120 adapted to receive a fluid-containing reservoir 105. FIG. 2 illustrates a cross-sectional view of the infusion pump 100 that illustrates the relationship between the drive system 108, the slide 106, the reservoir 105, and the sensor assembly 110 when assembled with the reservoir 105 inserted in the housing 102. It should be appreciated that FIGS. 1-2 depict the infusion pump 100 in a simplified manner; in practice, the infusion pump 100 could include additional elements, features, or components that are not shown or described in detail here.

The housing 102 is formed from a substantially rigid material having a hollow interior 114 adapted to allow the electronics assembly 104, reservoir 105, slide 106, drive system 108, sensor assembly 110, and capping member 112 to be disposed therein and enclosed by bottom portion 116. In the illustrated embodiment, the opening 120, the slide 106, and the drive system 108 are coaxially aligned in an axial direction (indicated by arrow 118). As described in greater detail below, the drive system 108 facilitates displacement of the slide 106 in the axial direction 118 to dispense fluid from the reservoir 105 (after the reservoir 105 has been inserted into opening 120), wherein the sensor assembly 110 is configured to measure axial forces (e.g., forces aligned with the axial direction 118) exerted on the sensor assembly 110. In various embodiments, the sensor assembly 110 may be utilized to detect one or more of the following: an occlusion in a fluid path that slows, prevents, or otherwise degrades fluid delivery from the reservoir 105 to a user's body; when the reservoir 105 is empty; when the slide 106 is properly seated with the reservoir 105; when a fluid dose has been delivered; when the infusion pump 100 is subjected to shock or vibration; when the infusion pump 100 requires maintenance.

In the illustrated embodiment, the electronics assembly 104 includes control electronics 124 coupled to a display element 126. In an exemplary embodiment, the display 126 is realized as a liquid crystal display (LCD), however, in alternative embodiments, the display 126 may be realized using another suitable display element. The display 126 may be utilized to present various types of information or data to the user, such as, without limitation: the current glucose level of the patient; the time; a graph or chart of the patient's glucose level versus time; device status indicators; alert messages; visual alert indicators; etc. The housing 102 includes a transparent window portion 128 that is aligned with the display 126 to allow the display 126 to be viewed by the user when the electronics assembly 104 is disposed within the interior 114 of the housing 102.

The control electronics 124 generally represent the hardware, firmware, processing logic and/or software (or combinations thereof) configured to control operation of the drive system 108 in a manner that is influenced by signals measured by and/or received from the sensor assembly 110 that are indicative of the axial force imparted to the sensor assembly 110. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 124 includes one or more programmable controllers that may be programmed to control operation of the infusion pump 100.

As illustrated in FIG. 1, the infusion pump 100 also includes a human-machine interface (HMI) 130 (or user interface) that is integral with or otherwise coupled to the housing 102. In an exemplary embodiment, the HMI 130 comprises HMI elements, such as buttons 132 and a directional pad 134, that are formed on a graphic keypad overlay 131 that overlies a keypad assembly 133, which includes features corresponding to the buttons 132, directional pad 134 or other user interface items indicated by the graphic keypad overlay 131. When assembled, the keypad assembly 133 is coupled to the control electronics 124, thereby allowing the HMI elements 132, 134 to be manipulated by the user to interact with the control electronics 124 and control operation of the infusion pump 100, for example, to administer a bolus of insulin, to change therapy settings, to change user preferences, to select display features, to set or disable alarms and reminders, and the like. In this regard, the control electronics 124 maintains and/or provides information to the display 126 regarding program parameters, delivery profiles, pump operation, alarms, warnings, statuses, or the like, which may be adjusted using the HMI elements 132, 134. In various embodiments, the HMI elements 132, 134 may be realized as physical objects (e.g., buttons, knobs, joysticks, and the like) or virtual objects (e.g., using touch-sensing and/or proximity-sensing technologies). For example, in some embodiments, the display 126 may be realized as a touch screen or touch-sensitive display, and in such embodiments, the features and/or functionality of the HMI elements 132, 134 may be integrated into the display 126 and the HMI 130 may not be present. In some embodiments, the electronics assembly 104 may also include alert generating elements coupled to the control electronics 124 and suitably configured to generate one or more types of feedback, such as, without limitation: audible feedback; visual feedback; haptic (physical) feedback; or the like.

Depending on the embodiment, the fluid-containing reservoir 105 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. The reservoir 105 typically includes a reservoir barrel 119 that contains the fluid and is concentrically and/or coaxially aligned with the slide 106 (e.g., in the axial direction 118) when the reservoir 105 is inserted into the infusion pump 100. The end of the reservoir 105 proximate the opening 120 may include a suitably configured fitting 123 (or cap) that secures the reservoir 105 in the housing 102, and which prevents displacement of the reservoir 105 in the axial direction 118 with respect to the housing 102 after the reservoir 105 is inserted into the housing 102. In an exemplary embodiment, the fitting 123 and/or reservoir 105 is configured to facilitate a fluid path from the reservoir 105 to a user. In this regard, a portion of the fitting 123 may extend through the opening 120 of the housing 102 and mate with tubing 121, thereby establishing fluid communication from the interior of the reservoir 105 and into the tubing 121 in a conventional manner. The tubing 121 may extend to an infusion set, which provides a fluid path to/from the body of the user. The opposing end of the reservoir 105 proximate the slide 106 includes a stopper 117 (or plunger) positioned to push fluid from inside the barrel 119 of the reservoir 105 along a fluid path through tubing 121 to a user. The slide 106 is configured to mechanically couple or otherwise engage with the stopper 117, thereby becoming seated with the stopper 117 and/or reservoir 105. As described in greater detail below in the context of FIG. 2, fluid is forced from the reservoir 105 via tubing 121 as the drive system 108 is operated to displace the slide 106 in the axial direction 118 toward the opening 120 in the housing 102.

In an exemplary embodiment, the drive system 108 includes a motor assembly 107 and a drive screw 109. The motor assembly 107 generally represents a motor and associated drive train components that convert rotational motor motion to a translational displacement of the slide 106 in the axial direction 118, and thereby engaging and displacing the stopper 117 of the reservoir 105. In some embodiments, the motor assembly 107 may also be powered to translate the slide 106 in the opposing direction (e.g., the direction opposite direction 118) to retract and/or detach from the reservoir 105 to allow the reservoir 105 to be replaced. In an exemplary embodiment, the motor assembly 107 includes a brushless DC motor, however, in other embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 105.

As best shown in FIG. 2, the drive screw 109 mates with threads 202 internal to the slide 106. When the motor assembly 107 is powered, the drive screw 109 rotates, and the slide 106 is forced to translate in the axial direction 118. In an exemplary embodiment, the infusion pump 100 includes a sleeve 111 to prevent the slide 106 from rotating when the drive screw 109 of the drive system 108 rotates. Thus, rotation of the drive screw 109 causes the slide 106 to extend or retract relative to the drive motor assembly 107. When the fluid infusion device is assembled and operational, the slide 106 contacts the stopper 117 to engage the reservoir 105 and control delivery of fluid from the infusion pump 100. In an exemplary embodiment, the shoulder portion 115 of the slide 106 contacts or otherwise engages the stopper 117 to displace the stopper 117 in the axial direction 118. In alternative embodiments, the slide 106 may include a threaded tip 113 capable of being detachably engaged with internal threads 204 on the stopper 117 of the reservoir 105, as described in detail in U.S. Pat. Nos. 6,248,093 and 6,485,465, which are incorporated by reference herein.

As shown in FIG. 1, the drive system 108 includes one or more electrical leads 136 adapted to be electrically coupled to the electronics assembly 104 to establish communication between the control electronics 124 and the drive system 108. In response to command signals from the control electronics 124 that regulate the amount of power supplied to the motor from a power supply, the motor actuates the drive train components to displace the slide 106 to force fluid from the reservoir 105, along a fluid path (including tubing 121 and an infusion set), thereby administering doses of the fluid contained in the reservoir 105 into the user's body. Preferably, the power supply is one or more batteries contained within the housing 102. Alternatively, the power supply may be a solar panel, capacitor, AC or DC power supplied through a power cord, or the like. In some embodiments, the control electronics 124 may operate the motor of the drive system 108 in a stepwise manner, typically on an intermittent basis; to administer discrete precise doses of the fluid to the user according to programmed delivery profiles. In alternative embodiments, the control electronics 124 may operate the motor continuously.

In an exemplary embodiment, the sensor assembly 110 includes a back plate structure 150 and a loading element 160. The back plate structure 150 is preferably affixed, adhered, mounted, or otherwise mechanically coupled to the bottom surface 138 of the drive system 108. Alternatively, the back plate structure 150 could be mounted to a different component of the infusion pump 100, such as the housing 102, a support structure, or any feature such that the back plate structure 150 resides between the bottom surface 138 of the drive system 108 and the bottom portion 116. The loading element 160 is disposed between the capping member 112 and a beam structure 170. The capping member 112 is contoured to accommodate and conform to the bottom of the sensor assembly 110 and the drive system 108. The capping member 112 is affixed to the interior of the housing 102 and prevents displacement of the sensor assembly 110 in the direction opposite the direction of force provided by the drive system 108 (e.g., the direction opposite direction 118).

As best illustrated by FIG. 2, the sensor assembly 110 is positioned between the motor assembly 107 and secured by the capping member 112 which is configured to prevent displacement of the sensor assembly 110 in a downward direction opposite the direction of arrow 118. Thus, the sensor assembly 110 is subjected to a reactionary compressive force when the drive system 108 and/or motor assembly 107 is operated to displace the slide 106 in the axial direction 118 in opposition to the fluid pressure in the reservoir 105. For example, if an occlusion developed within the fluid path, blocking fluid delivery from the infusion pump 100 to the body of the user, the fluid pressure would increase as the slide 106 is forced forward in the axial direction 118 by the drive system 108. Each time the control electronics 124 commands power to be supplied to the drive system 108, the slide 106 is driven forward into the reservoir 105, therefore increasing the fluid pressure in the reservoir 105. The fluid pressure is exerted against the slide 106, forcing it to back out of the reservoir 105; however, the drive system 108 prevents the slide 106 from retracting and the capping member 112 prevents displacement of the sensor assembly 110, thereby transferring the resultant force to the sensor assembly 110. Thus, under normal operating conditions the compressive force applied to the sensor assembly 110 by the drive system 108 and/or capping member 112 is correlated with the fluid pressure in the reservoir 105. As shown, electrical leads 140 are adapted to electrically couple the sensing elements of the sensor assembly 110 to the electronics assembly 104 to establish communication to the control electronics 124, wherein the control electronics 124 are configured to measure, receive, or otherwise obtain electrical signals from the sensing elements of the sensor assembly 110 that are indicative of the force applied by the drive system 108 in the axial direction 118, as described in greater detail below.

First Embodiment

FIGS. 3-6 depict an exemplary embodiment of a sensor assembly 300 suitable for use as the sensor assembly 110 of FIG. 1. The illustrated embodiment of the sensor assembly 300 includes a back plate structure 350 (also referred to herein as a back plate 350), a loading structure 360 (also referred to herein as a loading element), and a beam structure 370 disposed between the back plate 350 and the loading element 360. The beam structure 370 includes one or more beams 302 mechanically coupled to the loading element 360, such that a compressive force applied to the loading element 360 towards the back plate 350 deflects the beams 302 towards the back plate 350 until the inner portion 318 of the beams 302 contact the back plate 350. Each beam 302 has a sensing element 304 disposed thereon, wherein an electrical characteristic of the sensing element 304 is influenced by the amount of deflection of the respective beam 302, and thus, is indicative of the force applied to the sensor assembly 300, as described in greater detail below.

The back plate 350 comprises a rigid plate-like structure. In this regard, the back plate 350 has a substantially planar surface 310 and is comprised of a rigid material, such as carbon, steel, or another suitable material.

Figure 4:
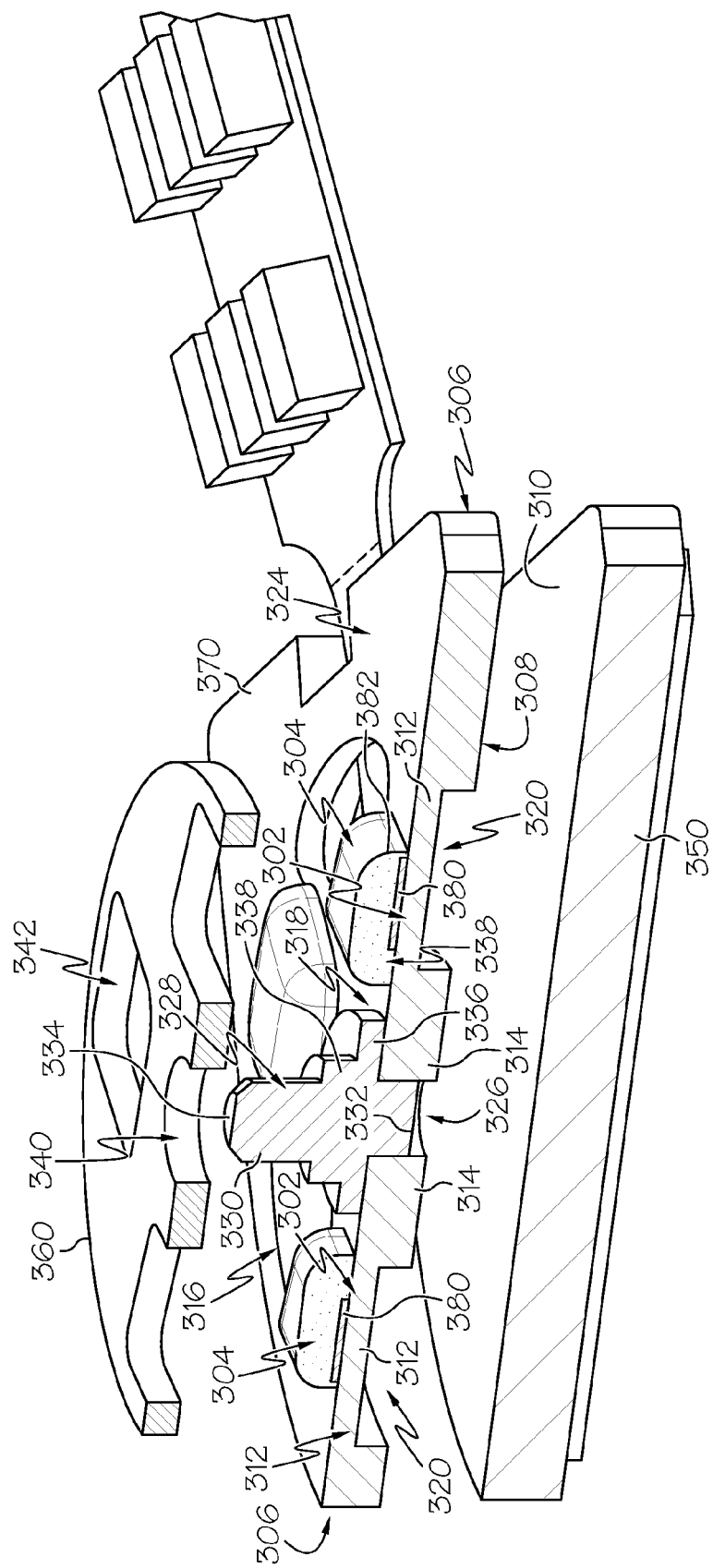
FIG. 4 is an exploded perspective view of the sensor assembly of FIG. 3 illustrating a partial cross-section of the sensor assembly as viewed along line 4-4 in FIG. 3.

In certain embodiments, the beam structure 370 is realized as a flexible metallic material, although in other embodiments, another deflectable material with desirable durability and aging characteristics may be used. As best shown in FIG. 4, an outer portion 306 of the beam structure 370 has a substantially planar surface 308 disposed adjacent to and in contact with the planar surface 310 of the back plate 350. The outer portion 306 of the beam structure 370 may be affixed, adhered, welded or otherwise mounted to the planar surface 310 about the periphery of the back plate 350. Thus, the outer portion 306 is supported by the back plate 350 and comprises a supported portion of the beam structure 370. In some embodiments, the outer portion 306 of the beam structure 370 may be integral with the back plate 350. In an exemplary embodiment, the outer portion 306 provides a substantially uniform thickness about the periphery of the beam structure 370. The thickness of the outer portion 306 of the beam structure 370 may vary depending on the needs of a particular embodiment.

Figure 5:
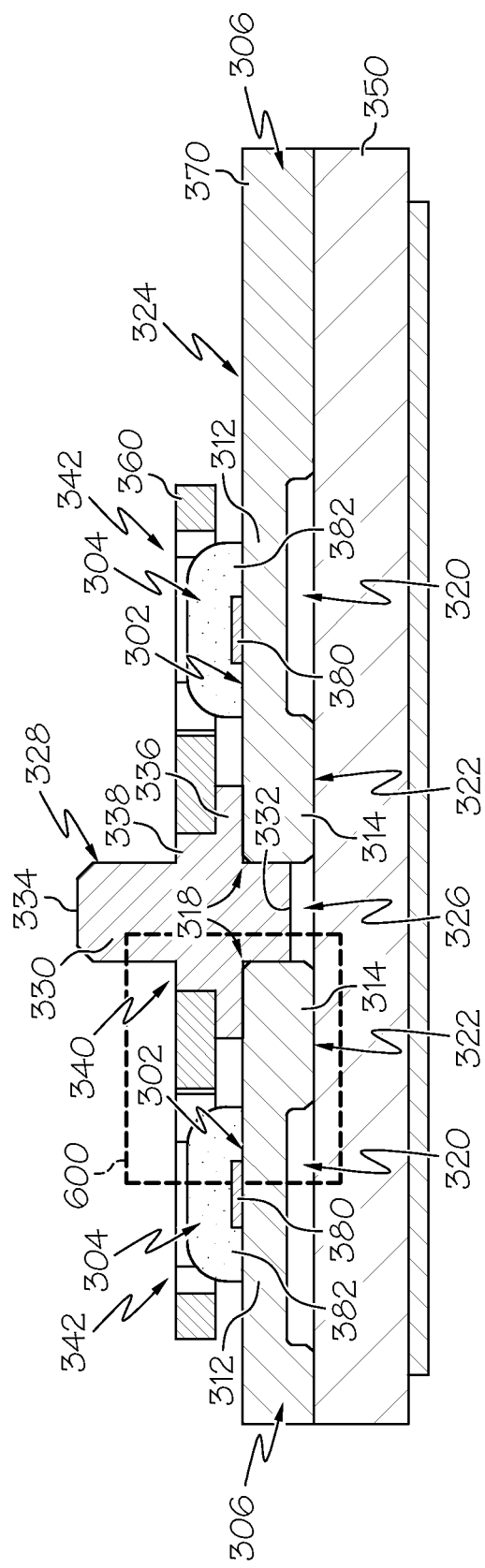
FIG. 5 is a cross-sectional view of the sensor assembly of FIG. 3 illustrating a cross-section as viewed along line 4-4 in FIG. 3.
Figure 6:
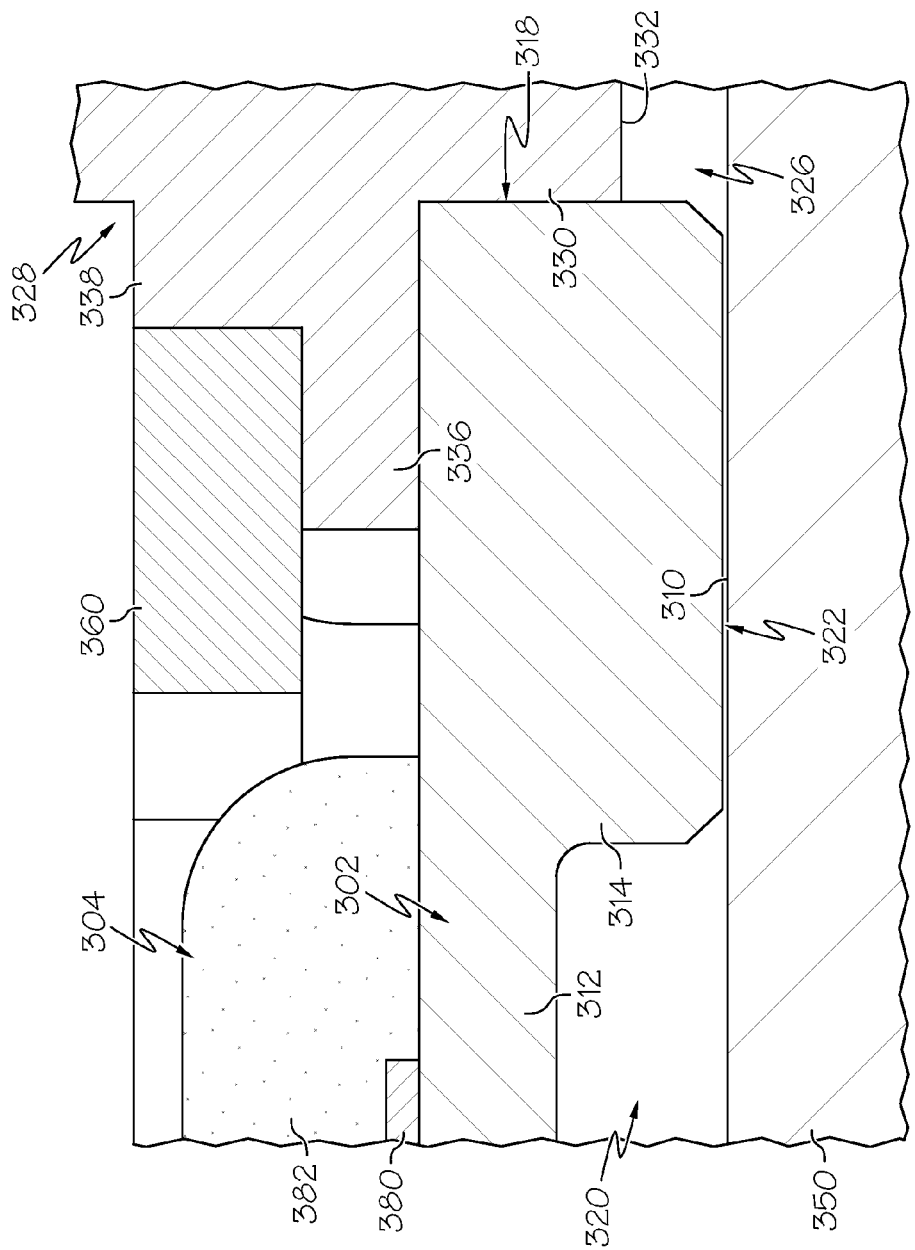
FIG. 6 is an enlarged cross-sectional view of a portion of the sensor assembly of FIGS. 3-5.

As best shown in FIGS. 4-5, each beam 302 comprises an arm portion 312 of the beam structure 370 that extends radially inward from the outer portion 306 to an end portion 314. Voided (or cutout) regions 316 are formed in the beam structure 370 adjacent to the arm portions 312 of the beams 302, such that the each voided region 316 physically separates arm portions 312 of adjacent beams 302. The arm portions 312 are configured to provide voided regions 320 between the beams 302 and the surface 310 of the back plate 350 such that the arm portions 312 are physically separated from the back plate 350. The end portions 314 of the beams 302 are configured such that in the absence of a compressive force applied to the back plate 350 and/or loading element 360, the end portions 314 do not contact the back plate 350. As best shown by the detailed view of region 600 in FIG. 6, the end portions 314 are configured to provide an airgap 322 separating the end portions 314 of the beams 302 from the surface 310 of the back plate 350. In this manner, the arm portions 312 and the end portions 314 are freestanding, detached, or otherwise separated from the back plate 350. The separation distance between the end portions 314 and the surface 310 of the back plate 350 provided by the airgap 322 is less than the separation distance between the arm portions 312 and the back plate 350 provided by the voided regions 320. In the illustrated embodiment, the end portions 314 of the beams 302 are integral and form an inner portion 318 of the beam structure 370. In one embodiment, the inner portion 318 is coaxially aligned with a drive system (e.g., drive system 108 in the axial direction 118).

Figure 3:
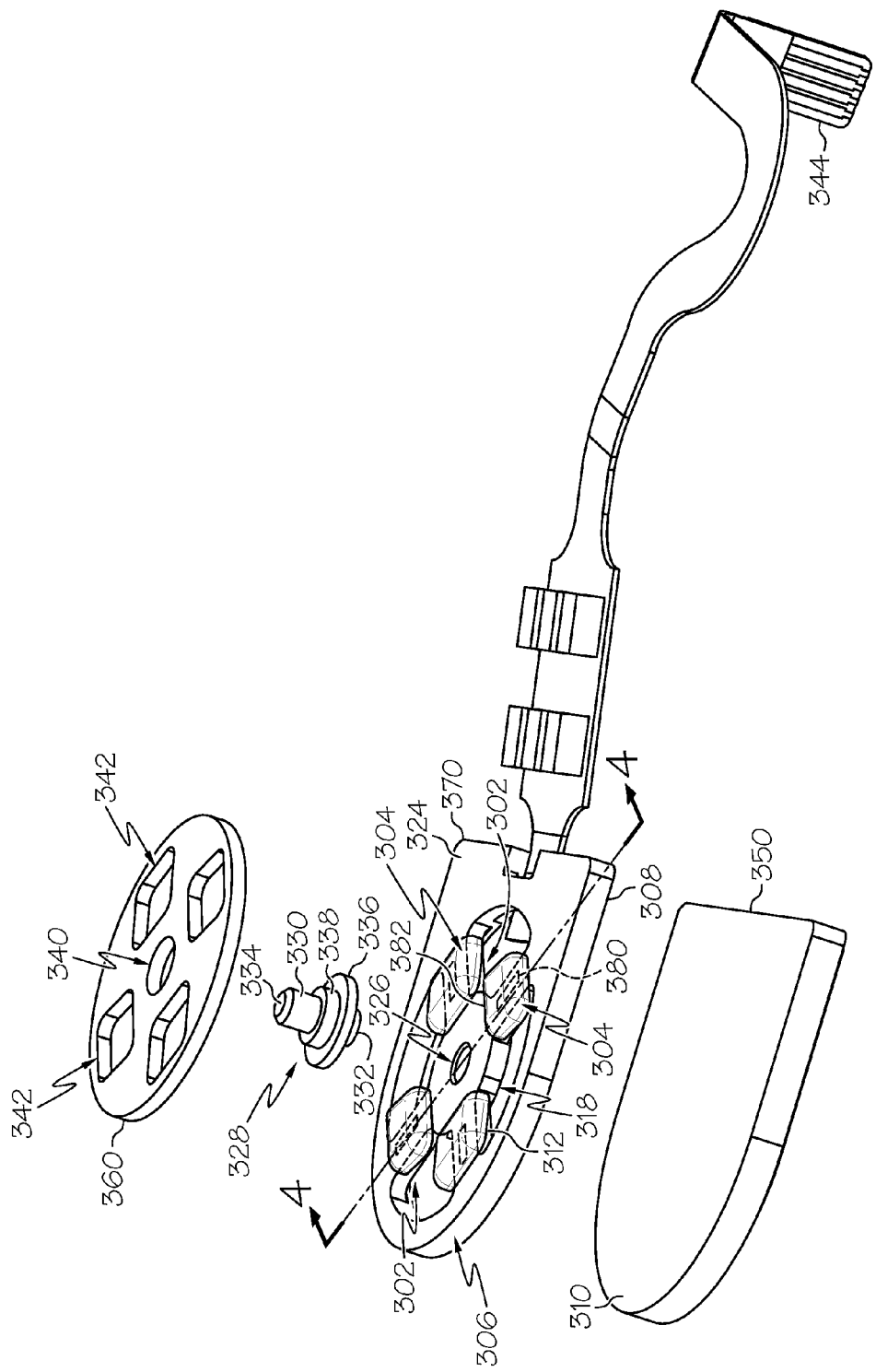
FIG. 3 is an exploded perspective view of an exemplary embodiment of a sensor assembly suitable for use with the infusion pump of FIG. 1.

As best shown in FIGS. 3-5, the inner portion 318 includes a circular opening 326 formed in the center of the inner portion 318 and adapted to receive a dowel member 328 that mechanically couples the beams 302 to the loading element 360. In the illustrated embodiment, the dowel member 328 includes a cylindrical portion 330 having a circumference that is less than the circumference of the opening 326 such that an end 332 of the cylindrical portion 330 is capable of being inserted into the opening 326. An opposing end 334 of the cylindrical portion 330 protrudes through an opening in the loading element 360 to align the sensor assembly 300 with an opening in a capping member (e.g., capping member 112), as described in greater detail below. In an exemplary embodiment, the dowel member 328 includes an outer circular rim portion 336 having a circumference that is greater than the circumference of the opening 326, such that the rim portion 336 overlaps the inner portion 318 of the beam structure 370 and prevents displacement of the dowel member 328 towards the back plate 350 with respect to the beam structure 370. Thus, the rim portion 336 distributes a compressive force applied to the sensor assembly 300 across the beams 302 in a substantially even manner. In some embodiments, the rim portion 336 is affixed, adhered, welded, or otherwise mounted to the inner portion 318 such that the dowel member 328 is fixed with respect to the inner portion 318 of the beam structure 370. In the illustrated embodiment, the outer circumference of the rim portion 336 is less than the outer circumference of the inner portion 318 of the beam structure 370, such that the rim portion 336 does not overlap or otherwise contact the arm portions 312 of the beams 302, however, in other embodiments, the outer circumference of the rim portion 336 may be greater than the outer circumference of the inner portion 318 and overlap at least some of the arm portions 312 of the beams 302. The length of the portion of the cylindrical portion 330 that extends from the outer circular rim portion 336 to the end 332 proximate the back plate 350 is less than the thickness of the end portions 314, such that the end 332 of the dowel member 328 does not contact the surface 310 of the back plate 350 before the end portions 314 contact the back plate 350. The dowel member 328 also includes an inner circular rim portion 338 having a circumference that is greater than the circumference of the cylindrical portion 330 but less than the circumference of the outer circular rim portion 338 for seating the loading element 360, as described below.

As best shown in FIGS. 3-5, the arm portion 312 of each beam 302 has a sensing element 304 disposed thereon. In an exemplary embodiment, each sensing element 304 is realized as a strain-sensitive element 380, such as a strain gauge, wherein deflection of the beam 302 produces a strain and corresponding change in an electrical characteristic of the strain-sensitive element. For example, a strain-sensitive element 380 may be realized as a serpentine wire or another patterned conductor rigidly joined to a surface of a beam 302, such that deflection of the beam 302 produces a strain and corresponding change in the resistance of the wire. In an exemplary embodiment, each strain-sensitive element 380 is realized as a patterned conductor printed on a substrate that is affixed to the surface 324 of the arm portion 312 of the respective beam 302, that is, the surface of the arm portions 312 opposite the surface 308 of the beam structure 370 that is affixed to the back plate 350. The strain-sensitive elements 380 may be adhered to the beams 302 by applying a glass coating that adheres the substrate to the beams 302. In an exemplary embodiment, a gel coating 382 (illustrated as being transparent in FIG. 3) is applied to the strain-sensitive elements 380 to prevent oxidation of the glass coating that adheres the strain-sensitive elements 380 to the beams 302. The gel coating 382 may also act as a dampener during an overload condition (e.g., in response to the infusion pump 100 being dropped or shaken) to prevent applied forces exceeding the intended measurement range of the sensor assembly 300 from being transferred directly to the strain-sensitive elements 380. Because the strain-sensitive elements 380 are rigidly affixed to the arm portions 312, deflection exhibited by the arm portions 312 is directly transferred to the strain-sensitive elements 380. Electrical leads 344 are electrically coupled to the strain-sensitive elements 380 and electrically couple the strain-sensitive elements 380 to control electronics (e.g., control electronics 124) configured to obtain or otherwise receive electrical signals from the strain-sensitive elements 380 that are indicative of the amount of force applied to sensor assembly 300, as described in greater detail below. In an exemplary embodiment, the strain-sensitive elements 380 are electrically configured to provide a Wheatstone bridge circuit that is utilized to determine the force applied to the sensor assembly 300 based on the resistances of strain-sensitive elements 380.

In the illustrated embodiment, the loading element 360 is realized as a circular disc-like structure having an outer circumference that is less than the inner circumference of the outer portion 306 of the beam structure 370 to prevent the loading element 360 from contacting the outer portion 306 of the beam structure 370 when the beams 302 are deflected towards the back plate 350. Accordingly, for convenience, the loading element 360 may alternatively be referred to herein as a loading disc. As best shown in FIG. 3, in an exemplary embodiment, the loading disc 360 includes a circular opening 340 disposed at the center of the loading disc 360 to align the loading disc 360 with the dowel member 328. The circumference of the opening 340 is greater than the circumference of the inner circular rim portion 338 but less than the circumference of the outer circular rim portion 336 to allow the loading disc 360 to be seated on the dowel member 328. In this manner, the outer circular rim portion 338 mechanically couples but physically separates the loading disc 360 and the end portions 314 and/or inner portion 318 of the beam structure 370, as shown by FIG. 5. In an exemplary embodiment, the opening 340 in the loading disc 360 is configured to be flush with the inner rim portion 338 to limit, prevent, or otherwise restrict radial displacement of the loading disc 360 with respect to the dowel member 328 in a drop or shock condition. The loading disc 360 includes a plurality of voided (or cutout) regions 342 aligned with the sensing elements 304 and configured such that the loading disc 360 does not contact the sensing elements 304. The loading disc 360 comprises a rigid material that does not substantially compress under the range of forces to be measured by the sensor assembly 300. The loading disc 360 is subjected to forces that exceed the intended measurement range for the sensor assembly 300, as described below. The thickness of the loading disc 360 is chosen to be as thin as possible while retaining sufficient rigidity to ensure that compressive forces applied to the sensor assembly 300 are transferred to the inner portion 318 of the beams 302.

By virtue of the separation between the beams 302 and the back plate 350, the beams 302 form deflectable portions of the beam structure 370 that exhibit deflection in response to compressive forces applied to the sensor assembly 300. The beams 302 are configured such that the end portions 314 of the beams 302 contact the surface 310 of the back plate 350 when a compressive force applied to the sensor assembly 300 is greater than a threshold value, thereby limiting, preventing, or otherwise inhibiting additional deflection of the arm portions 312 of the beams 302. In this regard, the separation distance provided by the airgap 322 and the flexion of the arm portions 312 are calibrated or otherwise configured to establish an upper limit on the compressive force that the beams 302 are subjected to. The threshold value is chosen to be greater than or equal to the upper end of the intended measurement range for the sensor assembly 300. In this manner, the threshold value is indicative of an overload condition, that is, an event that would result in the sensor assembly 300 being subjected to compressive forces exceeding the intended measurement range, for example, in the event a device including the sensor assembly 300 (e.g., infusion pump 100) is dropped. Thus, the threshold value corresponds to an upper limit on the amount of deflection that the beams 302 and/or sensing elements 304 are subjected to and protects the sensing elements 304 and the beams 302 from compressive forces exceeding the intended measurement range.

When the compressive force applied to the sensor assembly 300 is less than the threshold value, the beams 302 are freely movable (or deflectable) with respect to the back plate 350 and the back plate 350 does not influence the deflection of the beams 302. A compressive force applied to the sensor assembly 300 that is less than the threshold value causes deflection of the arm portions 312 of the beams 302, thereby reducing the separation distance between the end portions 314 and the surface 310 of the back plate 350 (e.g., reducing the size of the airgap 322) and producing a corresponding change in the electrical characteristic of the sensing elements 304. A force applied to the sensor assembly 300 that is equal to the threshold value causes the end portions 314 to contact the surface 310 of the back plate 350, wherein the rigid material of the back plate 350 provides support and prevents further displacement of the end portions 314 towards the back plate 350. Thus, the deflection of the arm portions 312 does not increase in response to additional force applied to the sensor assembly 300 and is limited to an amount corresponding to the separation distance of the airgap 322. Any additional compressive force applied to the sensor assembly 300 is distributed across the back plate 350, the loading disc 360, the end portions 314 and/or the outer portion 306 of the beam structure 370, thereby limiting, preventing, or otherwise inhibiting additional deflection of the arm portions 312.

In accordance with one or more embodiments, the sensor assembly 300 is intended to measure forces between 0 pounds (0 N) and 5.0 pounds (22.2 N) with the desired resolution of less than or equal to 0.01 pounds (0.04 N). The threshold value for a compressive force that achieves sufficient deflection of the beams 302 such that the end portions 314 contact the surface 310 of the back plate 350 may be chosen to be a force value greater than the upper end of the intended measurement range that is sufficiently likely to compromise the structural integrity of the beams 302 and/or arm portions 312, strain gauges 380, the beam structure 370, and/or another member of the sensor assembly 300. For example, the threshold value for a compressive force may be chosen to be about one hundred percent to about two hundred percent of the upper end of the intended measurement range. In one embodiment, where the intended measurement range for the sensor is between 0 pounds (0 N) and 5.0 (22.2 N) pounds of force with the desired resolution of less than or equal to 0.01 pounds (0.04 N), and the beams 302 and/or airgaps 322 are calibrated to provide a threshold force value of about 7.0 pounds (31.1 N).

Referring again to FIGS. 1-2, and with continued reference to FIGS. 3-6, in an exemplary embodiment, sensor assembly 110 is realized as the sensor assembly 300 of FIG. 3. As shown in FIG. 1, the capping member 112 includes an opening 142 adapted to allow the end 334 of the dowel member 328 that protrudes through the loading disc 360 to be inserted into the capping member 112. Thus, the capping member 112 prevents lateral displacement of the dowel member 328, which in turn, limits, prevents, or otherwise restricts lateral displacement of the sensor assembly 300 with respect to the capping member 112. In accordance with one or more embodiments, the thickness of the loading disc 360 and the inner rim portion 338 are substantially equal to provide a continuous surface, such that the capping member 112 simultaneously contacts the loading disc 360 and the inner rim portion 338. In an exemplary embodiment, the opening 142 in the capping member 112, the opening 340 in the loading disc 360, the cylindrical portion 330 of the dowel member 328, and the circular opening 326 in the inner portion 318 of the beam structure 370 are concentrically aligned in the axial direction 118.

Depending on the embodiment, the back plate 350 may be affixed, adhered, mounted, or otherwise mechanically coupled to the bottom surface 138 of the drive system 108. When the drive system 108 drives the slide 106 forward into the reservoir 105 in the axial direction 118, fluid pressure increases, producing a reactionary force on the drive system 108 in the opposite direction which is transferred to the back plate 350. The capping member 112 prevents displacement of the sensor assembly 300 and effectively maintains the loading disc 360 and/or dowel member 328 in a fixed position with respect to the capping member 112 and/or housing 102. As a result, the reactionary force is transferred to the beams 302 by the loading disc 360 and/or rim portion 336 of the dowel member 328. In this manner, the capping member 112 is configured to deflect the beams 302 towards the surface 310 of the back plate 350 in response to the force provided by the drive system 108 in the axial direction 118. The deflection of the beams 302 is correlated with the axial force applied to the sensor assembly 300 and produces a corresponding increase in the strain exerted upon sensing elements 304. Thus, when the sensing elements 304 are each realized as strain-sensitive elements such as strain gauges, the resistance of the strain-sensitive elements 380 corresponds to or is otherwise correlated with the force applied by the drive system 108, which in turn corresponds to or is otherwise correlated with the fluid pressure in the reservoir 105.

The control electronics 124 are electrically coupled to the strain-sensitive elements 380 and configured to measure, receive, or otherwise obtain electrical signals from the strain-sensitive elements 380 that correspond to the resistance of the strain-sensitive elements 380. For example, the control electronics 124 may regulate the supply of an injection signal (e.g., a constant voltage or constant current) from a power supply for the infusion pump 100 to the strain-sensitive elements 380 and measure or otherwise obtain response signal (e.g., a measured current or voltage) caused by the injection signal, wherein the response signal is influenced by the resistance of the strain-sensitive elements 380 and therefore correlated with the fluid pressure of the reservoir 105 and/or force applied by the drive system 108 in the axial direction 118. For example, injecting a constant current signal will result in a measured voltage signal across the strain-sensitive elements 380 which is directly related to the resistance of the strain-sensitive elements 380, and therefore, is also directly related to the fluid pressure of the reservoir 105 and/or force applied by the drive system 108 in the axial direction 118. Conversely, injecting a constant voltage signal will result in a measured current signal through the strain-sensitive elements 380 which is inversely related to the resistance of the strain-sensitive elements 380, and therefore, is also inversely related to the fluid pressure of the reservoir 105 and/or force applied by the drive system 108 in the axial direction 118.

The control electronics 124 may utilize the relationship between the injection signal and the response signal to calculate, determine, or otherwise obtain values corresponding to the electrical characteristic of the sensing elements 304 that are influenced by the deflection of the beams 302. In this manner, the control electronics 124 may calculate or otherwise determine the force provided or otherwise applied by the drive system 108 in the axial direction 118 based upon the relationship between the injection signal the response signal. In some embodiments, the control electronics 124 may also calculate or otherwise determine the fluid pressure in the reservoir 105 based upon the force provided by the drive system 108 to displace the slide 106.

As set forth above, the control electronics 124 may be configured to modify or otherwise regulate the power provided to the drive system 108 and/or perform additional functions, operations, tasks, processes, and the like based upon the signals obtained from the sensor assembly 300. For example, in various embodiments, based upon the signals obtained from the sensor assembly 300, the control electronics 124 may be configured to perform one or more of the following: detect an occlusion in the fluid path from the reservoir 105 and/or infusion pump 100 to a user; detect when the slide 106 is properly seated with a stopper of the reservoir 105; detect the removal of one or more components in the fluid path such as disconnecting the infusion set, disconnecting the tubing, or the like; detect when the reservoir 105 is empty. Examples of actions that may be undertaken by the control electronics 124 are described in greater detail in U.S. Pat. No. 6,485,465, which is incorporated by reference herein.

Second Embodiment

Figure 7:
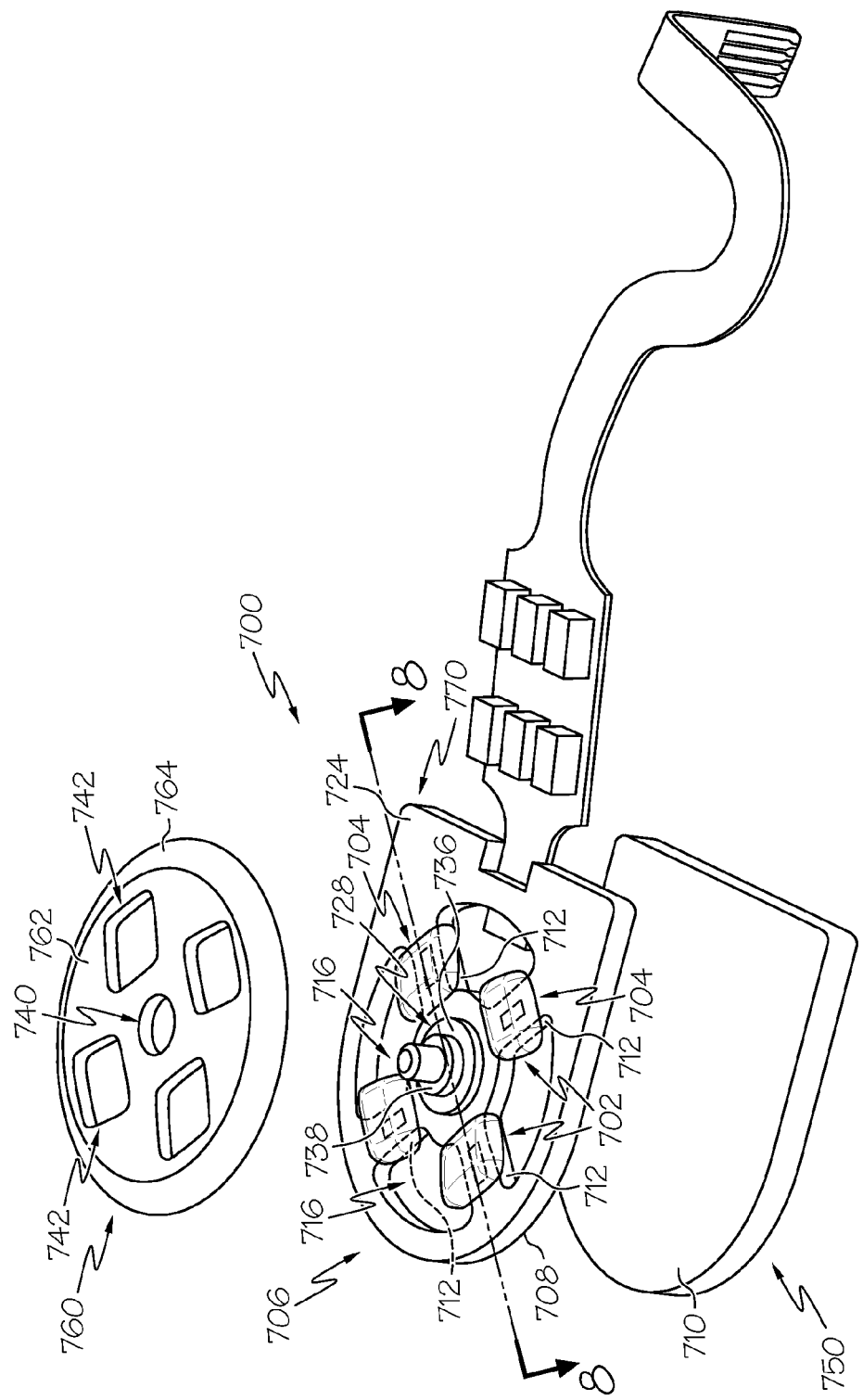
FIG. 7 is a perspective view of an another embodiment of a sensor assembly suitable for use with the infusion pump of FIG. 1.
Figure 8:
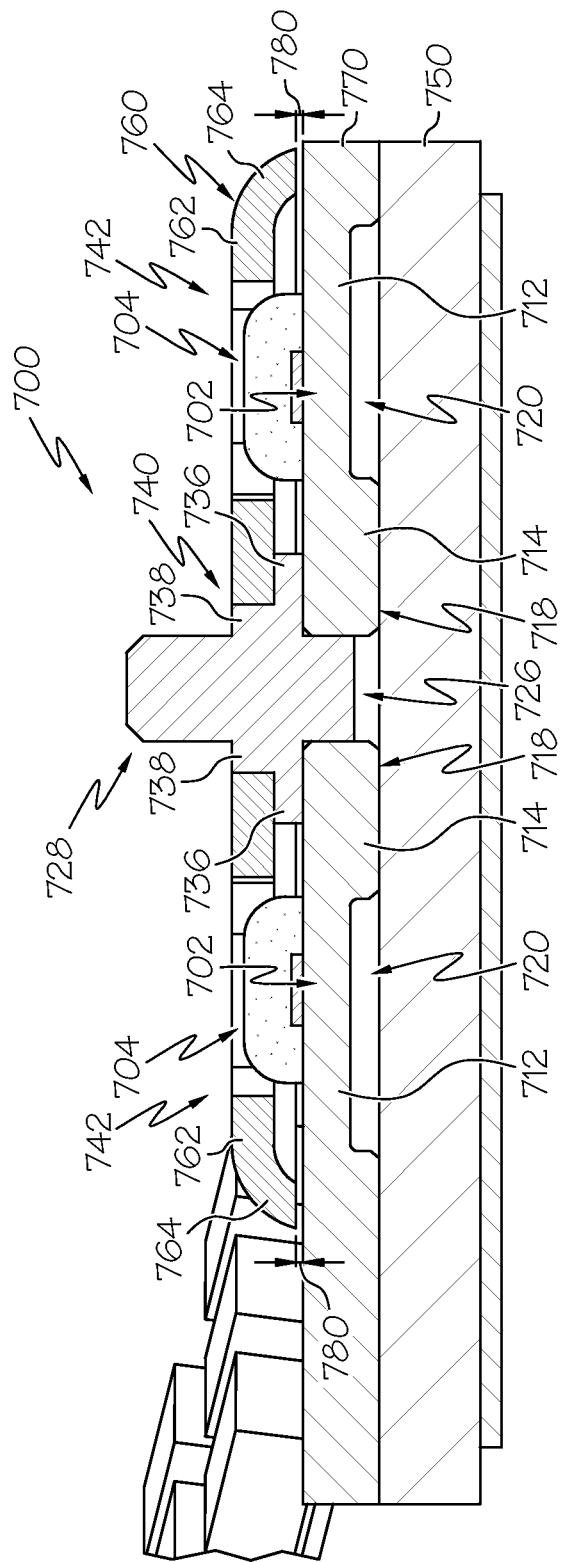
FIG. 8 is a cross-sectional view of the sensor assembly of FIG. 7 illustrating a cross-section as viewed along line 8-8 in FIG. 7.

FIGS. 7-8 depict another exemplary embodiment of a sensor assembly 700 suitable for use as the sensor assembly 110 of FIG. 1. The illustrated embodiment of the sensor assembly 700 includes a loading structure 760 (also referred to herein as a loading element), a back plate structure 750 (or back plate), and a beam structure 770 disposed between the back plate 750 and the loading element 760. Various elements of sensor assembly 700 are similar to counterpart elements described above in the context of sensor assembly 300 of FIGS. 3-6, and the common features of such elements will not be redundantly described here in the context of FIGS. 7-8. As described above in the context of FIGS. 3-6, the beam structure 770 includes one or more beams 702 mechanically coupled to the loading element 760, such that a compressive force applied to the loading element 760 towards the back plate 750 deflects the beams 702 towards the back plate 750. Each beam 702 has a sensing element 704 disposed thereon, wherein an electrical characteristic of the sensing element 704 is influenced by the amount of deflection of the respective beam 702, and thus, is indicative of the force applied to the sensor assembly 700. As described in greater detail below, the loading element 760 includes a feature 764 that prevents, inhibits, or otherwise limits deflection of the beams 702 when the compressive force applied to the sensor assembly 700 exceeds the intended measurement range for the sensor assembly 700.

As illustrated in FIGS. 7-8, the substantially planar surface 708 of the outer portion 706 of the beam structure 770 is disposed adjacent to and in contact with the planar surface 710 of the back plate 750, and the outer portion 706 may be affixed, adhered, welded or otherwise mounted to the planar surface 710 about the periphery of the back plate 750 to provide a supported portion of the beam structure 770 in a similar manner as described above in the context of FIGS. 3-6. Each beam 702 comprises an arm portion 712 of the beam structure 770 that extends radially inward from the supported outer portion 706 to an end portion 714. Voided regions 716 physically separate arm portions 712 of adjacent beams 702, and the arm portions 712 are configured to provide voided regions 720 between the beams 702 and the surface 710 of the back plate 750 such that the arm portions 712 are physically separated from the back plate 750. In the absence of a compressive force applied to the back plate 750 and/or loading element 760, the end portions 714 of the beams 702 do not contact the back plate 750 and the beams 702 are freestanding, detached, or otherwise separated from the back plate 750. In the illustrated embodiment, the end portions 714 of the beams 702 are integral to form an inner portion 718 of the beam structure 770 that is coaxially aligned with a drive system (e.g., drive system 108 in the axial direction 118). The inner portion 718 includes a circular opening 726 formed in the center of the inner portion and adapted to receive a dowel member 728 that mechanically couples the beams 702 to the loading element 760. A rim portion 736 of the dowel member 728 has a circumference that is greater than the circumference of the opening 726, such that the rim portion 736 overlaps the inner portion 718 of the beam structure 770 to prevent displacement of the dowel member 728 and/or loading element 760 towards the back plate 750 with respect to the inner portion 718 and distribute a compressive force applied to the sensor assembly 700 across the beams 702 in a substantially even manner.

Still referring to FIGS. 7-8, in an exemplary embodiment, the loading element 760 includes an inner planar portion 762 having a portion 764 that extends from the inner planar portion 762. In an exemplary embodiment, the extension portion 764 is realized as a curved or rounded portion about the periphery of the inner portion 762 that is curved or rounded towards the beam structure 770. In the illustrated embodiment, the inner portion 762 is realized as a circular disc-like structure having the rounded portion 764 circumscribing its perimeter. In this manner, the rounded portion 764 provides a curved rim about the periphery of the inner portion 762. For convenience, the loading element 760 may alternatively be referred to herein as a domed loading disc and the rounded or curved portion 764 of the disc-like structure 762 may alternatively be referred to herein as a shoulder portion. The loading disc 760 comprises a rigid material that does not substantially compress under the range of forces to be measured by the sensor assembly 700.

In a similar manner as described above, the domed loading disc 760 includes a circular opening 740 disposed at the center of the domed loading disc 760 to allow the loading disc 760 to be seated on the dowel member 728. In this manner, the substantially rigid rim portion 736 mechanically couples but physically separates the inner planar portion 762 of the domed loading disc 760 and the end portions 714 and/or inner portion 718, as best illustrated by FIG. 8. In an exemplary embodiment, the opening 740 in the loading disc 760 is configured to be flush with the dowel member 728 to limit, prevent, or otherwise restrict radial displacement of the domed loading disc 760 with respect to the dowel member 728. The domed loading disc 760 also includes a plurality of voided (or cutout) regions 742 aligned with the sensing elements 704 and configured such that the loading disc 760 does not contact the sensing elements 704.

As best illustrated in FIG. 8, the outer circumference of the domed loading disc 760 is greater than the inner circumference of the outer portion 706 of the beam structure 770 such that the shoulder portion 764 overlaps the outer portion 706 and is capable of contacting the outer portion 706 when the beams 702 are deflected towards the back plate 750. In an exemplary embodiment, the shoulder portion 764 of the domed loading disc 760 and the thickness of the rim portion 736 are configured to provide an airgap 780 separating the shoulder portion 764 from the surface 724 of the outer portion 706 of the beam structure 770.

By virtue of the separation between the beams 702 and the back plate 750, the beams 702 form deflectable portions of the beam structure 770 that exhibit deflection in response to compressive forces applied to the sensor assembly 700 that displace the inner portion 718 with respect to the supported outer portion 706. In an exemplary embodiment, the airgap 780 is configured such that the shoulder portion 764 of the domed loading disc 760 contacts the surface 724 of the outer portion 706 of the beam structure 770 when a compressive force applied to the sensor assembly 700 is greater than a threshold value. In this regard, the separation distance provided by the airgap 780 is calibrated or otherwise configured to establish an upper limit on the compressive force that the arm portions 712 of the beams 702 are subjected to. In an exemplary embodiment, the threshold value is chosen to be greater than or equal to the upper end of the intended measurement range for the sensor assembly 700. In this manner, the threshold value is indicative of an overload condition, that is, an event that would result in the sensor assembly 700 being subjected to compressive forces exceeding the intended measurement range, for example, in the event a device including the sensor assembly 700 (e.g., infusion pump 100) is dropped.

Due to the rigidity of the domed loading disc 760, when the shoulder portion 764 is in contact with the outer portion 706 of the beam structure 770, additional displacement of the inner portion 718 and/or end portions 714 towards the back plate 750 with respect to the outer portion 706 is inhibited, restricted or otherwise prevented. In this manner, the shoulder portion 764 of the domed loading disc 760 limits, prevents, or otherwise inhibits additional deflection of the arm portions 712 of the beams 702. Thus, the threshold value corresponds to an upper limit on the amount of deflection that the beams 702 and/or sensing elements 704 are subjected to and protects the sensing elements 704 and the beams 702 from compressive forces exceeding the intended measurement range. Additional compressive forces applied to the sensor assembly 700 exceeding the threshold value are transferred to the domed loading disc 760 and the outer portion 706 of the beam structure 770 and away from the beams 702. In this manner, the loading disc 760, the outer portion 706 of the beam structure 770 and/or the back plate 750 are subjected to forces that exceed the intended measurement range for the sensor assembly 700.

In a similar manner as described above, when the compressive force applied to the sensor assembly 700 is less than the threshold value, the beams 702 are freely movable (or deflectable) and the domed loading disc 760 does not influence the deflection of the beams 702. A compressive force applied to the sensor assembly 700 that is less than the threshold value causes deflection of the arm portions 712 of the beams 702, thereby reducing the separation distance between the shoulder portion 764 and the surface 724 of the outer portion 706 (e.g., reducing the size of the airgap 780) and producing a corresponding change in the electrical characteristic of the sensing elements 704. A force applied to the sensor assembly 700 that is equal to the threshold value causes the shoulder portions 764 to contact the surface 724 of the outer portion 706 of the beam structure 770, wherein the rigid material of the domed loading disc 760 provides support and prevents further displacement of the end portions 714 of the beams 702. Thus, the deflection of the arm portions 712 does not increase in response to additional force applied to the sensor assembly 700 and is limited to an amount corresponding to the separation distance of the airgap 780. Any additional compressive force applied to the sensor assembly 700 is distributed across the back plate 750, the domed loading disc 760, and the outer portion 706 of the beam structure 770, thereby limiting, preventing, or otherwise inhibiting additional deflection of the arm portions 712.

Referring again to FIGS. 1-2, and with continued reference to FIGS. 7-8, in accordance with one embodiment, sensor assembly 110 is realized as the sensor assembly 700 of FIGS. 7-8. As described above, the back plate 750 may be affixed, adhered, mounted, or otherwise mechanically coupled to the bottom surface 138 of the drive system 108 such that the sensor assembly 700 and the drive system 108 are concentrically aligned in the axial direction 118. When the drive system 108 drives the slide 106 forward into the reservoir 105 in the axial direction 118, fluid pressure increases, producing a reactionary force on the drive system 108 in the opposite direction which is transferred to the back plate 750. The capping member 112 prevents displacement of the sensor assembly 700 and effectively maintains the loading disc 760 and/or dowel member 728 in a fixed position with respect to the capping member 112 and/or housing 102. As a result, the reactionary force is transferred to the beams 702 by the loading disc 760 and/or rim portion 736 of the dowel member 728. In this manner, the capping member 112 is configured to deflect the beams 702 towards the surface 710 of the back plate 750 in response to the force provided by the drive system 108 in the axial direction 118. The deflection of the beams 702 is correlated with the axial force applied to the sensor assembly 700 and produces a corresponding increase in the strain exerted upon sensing elements 704. As set forth above, the control electronics 124 are electrically coupled to the sensing elements 704 and configured to determine the force provided or otherwise applied by the drive system 108 in the axial direction 118 based on electrical signals obtained from the sensing elements 704.

Referring now to FIGS. 3-8, in accordance with one or more embodiments, the loading disc 360 of the sensor assembly 300 may be realized as the domed loading disc 760 described above in the context of FIGS. 7-8. In such embodiments, the separation distance provided by airgap 780 may be substantially equal to the separation distance provided by the airgap 322 between the end portions 314 of the beam structure 370 and the surface 310 of the back plate 350. In such embodiments, in response to a compressive force applied to the sensor assembly exceeding the intended measurement range, the shoulder portion 764 of the domed loading disc 760 contacts the outer portion 306 of the beam structure 370 and the end portions 314 of the beams 302 contact the back plate 350 substantially simultaneously to distribute the load evenly across the beam structure 370.

Third Embodiment

Figure 9:
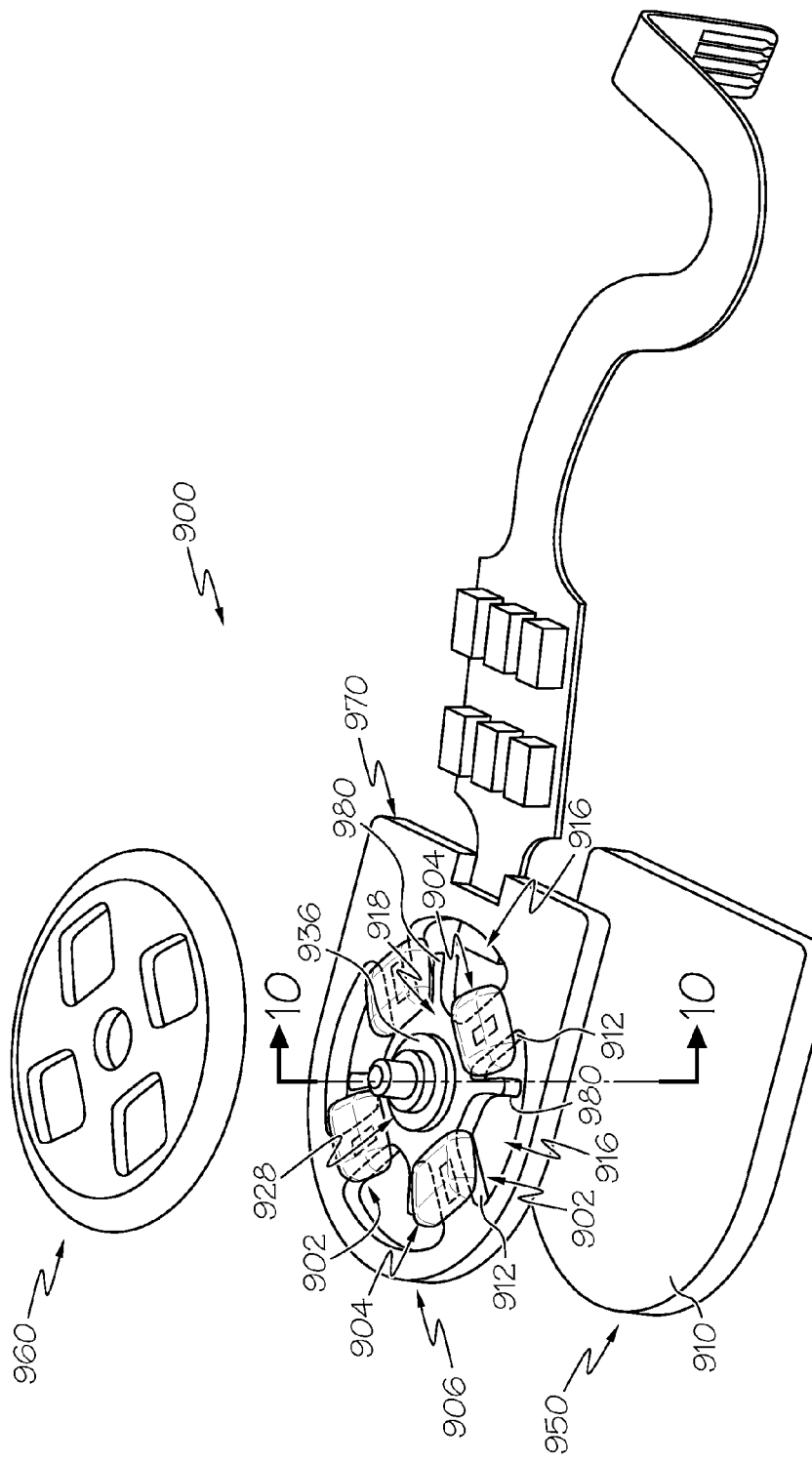
FIG. 9 is an exploded perspective view of an another embodiment of a sensor assembly suitable for use with the infusion pump of FIG. 1.
Figure 10:
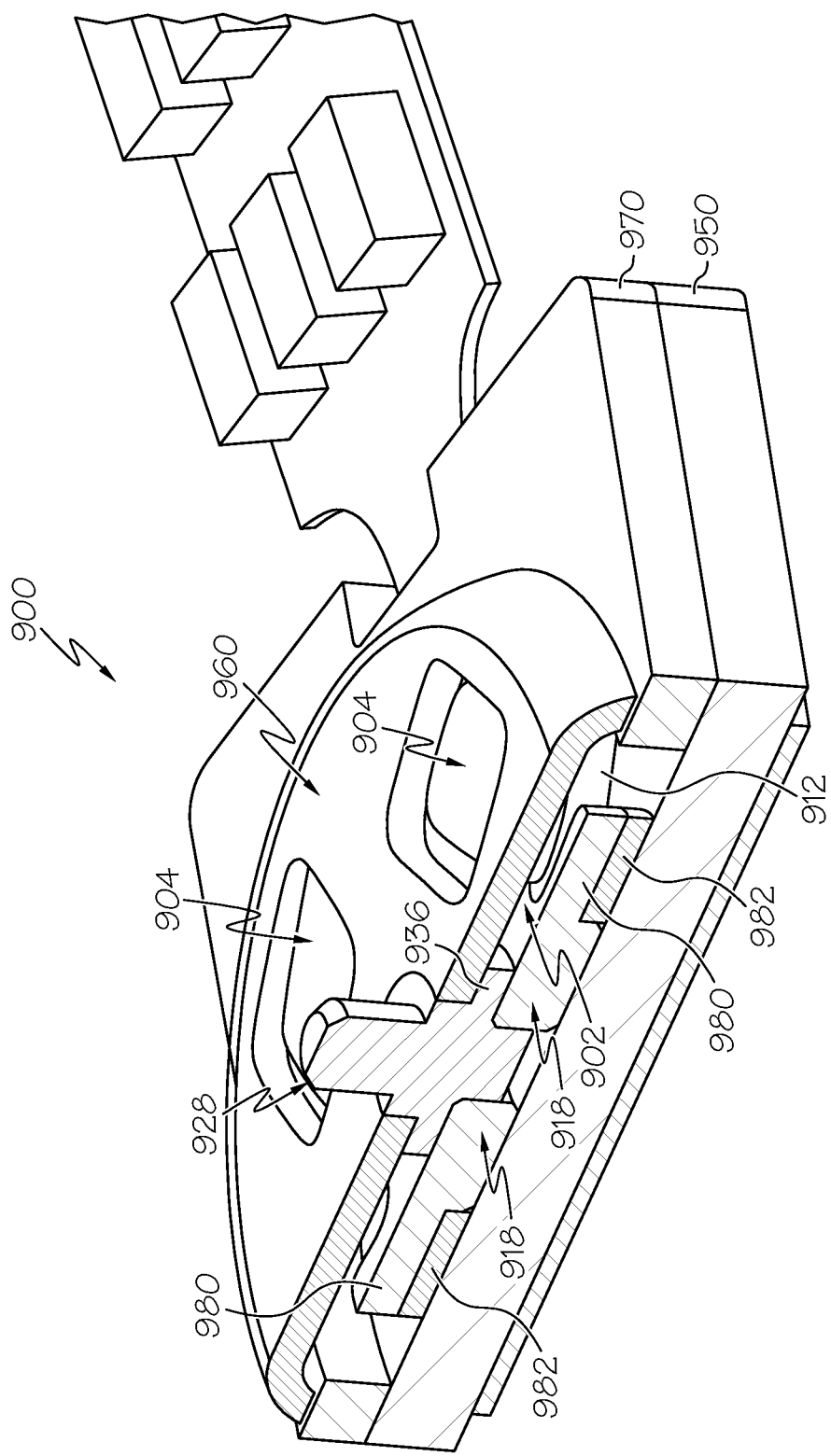
FIG. 10 is a cross-sectional view of the sensor assembly of FIG. 9 illustrating a cross-section as viewed along line 10-10 in FIG. 9.

FIGS. 9-10 depict another exemplary embodiment of a sensor assembly 900 suitable for use as the sensor assembly 110 of FIG. 1. The illustrated embodiment of the sensor assembly 900 includes a loading structure 960 (also referred to herein as a loading element), a back plate structure 950 (or back plate), and a beam structure 970 disposed between the back plate 950 and the loading element 960. Various elements of sensor assembly 900 are similar to counterpart elements described above in the context of sensor assembly 300 of FIGS. 3-6, and the common features of such elements will not be redundantly described here in the context of FIGS. 9-10. As described above in the context of FIGS. 3-6, the beam structure 970 includes one or more beams 902 mechanically coupled to the loading element 960, such that a compressive force applied to the loading element 960 towards the back plate 950 deflects the beams 902 towards the back plate 950. Each beam 902 has a sensing element 904 disposed thereon, wherein an electrical characteristic of the sensing element 904 is influenced by the amount of deflection of the respective beam 902, and thus, is indicative of the force applied to the sensor assembly 900. As described in greater detail below, the beam structure 970 includes cantilevered portions 980 configured to dampen or otherwise absorb impulse forces applied to the sensor assembly 900 that may otherwise result in potentially damaging deflection of the beams 902, for example, during a drop or shock condition.

As illustrated in FIGS. 9-10, the outer portion 906 of the beam structure 970 is disposed adjacent to and in contact with the planar surface 910 of the back plate 950, and the outer portion 906 may be affixed, adhered, welded or otherwise mounted to the planar surface 910 about the periphery of the back plate 950 to provide a supported portion of the beam structure 970 in a similar manner as described above in the context of FIGS. 3-6. Each beam 902 comprises an arm portion 912 of the beam structure 970 that extends radially inward from the outer portion 906 to an end portion. In the illustrated embodiment, the end portions of the beams 902 are integral to form an inner portion 918 of the beam structure 970 that is coaxially aligned with a drive system (e.g., drive system 108 in the axial direction 118). Voided regions 916 physically separate arm portions 912 of adjacent beams 902, and the arm portions 912 are configured to provide voided regions between the beams 902 and the surface 910 of the back plate 950 such that the arm portions 912 are physically separated from the back plate 950. In the absence of a compressive force applied to the back plate 950 and/or loading element 960, the inner portion 918 (i.e., the end portions of the beams 902) does not contact the back plate 950 and the beams 902 are freestanding, detached, or otherwise separated from the back plate 950. In a similar manner as described above, the inner portion 918 includes a circular opening adapted to receive a dowel member 928 that mechanically couples the end portions of the beams 902 to the loading element 960. A rim portion 936 of the dowel member 928 overlaps the inner portion 918 of the beam structure 970 to prevent displacement of the dowel member 928 and/or loading element 960 towards the back plate 950 with respect to the inner portion 918 and distribute a compressive force applied to the sensor assembly 900 across the beams 902 in a substantially even manner.

In the illustrated embodiment of FIGS. 9-10, the beam structure 970 includes a plurality of cantilevered portions 980 that extend radially outward from the inner portion 918 of the beam structure 970. As described in greater detail below, the cantilevered portions 980 are configured to dampen impulse forces applied to the sensor assembly 900 by dampening, retarding or otherwise slowing the rate of displacement of the inner portion 918, which in turn, reduces the rate of deflection of the beams 902. As best illustrated in FIG. 9, the cantilevered portions 980 protrude into the voided regions 916 between adjacent beams 902. In this regard, the cantilevered portions 980 are separated from arm portions 912 of adjacent beams 902 by portions of the voided regions 916. In an exemplary embodiment, the beam structure 970 includes the same number of beams 902 and cantilevered portions 980, such that each arm portion 912 is located between two adjacent cantilevered portions 980 while each cantilevered portion 980 is located between two adjacent arm portions 912. The cantilevered portions 980 are also separated from the outer portion 906 of the beam structure 970 by the voided regions 916, such the cantilevered portions 980 are movable with respect to the outer portion 906. In this regard, the radial length of the cantilevered portions 980 is less than the radial length of the arm portions 912. By virtue of their separation from the outer portion 906 and arm portions 912, the cantilevered portions 980 move in unison with the inner portion 918 and/or end portions of the beams 902 with respect to the outer portion 906.

As illustrated in FIG. 10, in an exemplary embodiment, the cantilevered portions 980 include a dampening material 982 configured to dampen, retard, or otherwise impede displacement of the inner portion 918 and/or end portions of the beams 902 with respect to the outer portion 906, and thereby mitigate or otherwise reduce the rate of deflection of the arm portions 912 of the beams 902. In an exemplary embodiment, the dampening material 982 is affixed to the lower surface of the cantilevered portions 980 and disposed between the lower surface of the cantilevered portions 980 and the surface 910 of the back plate 950. In the illustrated embodiment, the dampening material 982 contacts the surface 910 of the back plate 950, wherein the rigidity of the back plate 950 inhibits or otherwise prevents displacement of the dampening material 982, and as a result, the dampening material 982 absorbs impulse forces applied to the sensor assembly 900. In this manner, the dampening material 982 and cantilevered portions 980 protect the sensing elements 904 and the beams 902 from potentially damaging deflection that may otherwise result from compressive impulse forces that exceed the intended measurement range.

By virtue of the separation between the cantilevered portions 980 and the beams 902 and/or arm portions 912, the dampening material 982 does not influence deflection of the beams 902 and/or arm portions 912 when compressive forces within the intended measurement range are gradually applied to the sensor assembly 900. In this regard, the dampening material 982 and the cantilevered portions 980 are configured such that in response to compressive forces within the intended measurement range applied to the sensor assembly 900, any influence on the deflection of the beams 902 and/or the displacement of inner portion 918 attributable the cantilevered portions 980 and/or dampening material 982 is negligible. Thus, the beams 902 are freely movable (or deflectable) with respect to the back plate 950, and the inner portion 918 may be displaced with respect to the outer portion 906 towards the back plate 950 with negligible dampening or resistance attributable to the cantilevered portions 980 and/or dampening material 982, resulting in applied forces within the intended measurement range being effectively transferred directly to the beams 902.

Referring again to FIGS. 1-2, and with continued reference to FIGS. 9-10, in accordance with one embodiment, sensor assembly 110 is realized as the sensor assembly 900 of FIGS. 9-10. As described above, the back plate 950 may be affixed, adhered, mounted, or otherwise mechanically coupled to the bottom surface 138 of the drive system 108 such that the sensor assembly 900 and the drive system 108 are concentrically aligned in the axial direction 118. When the drive system 108 drives the slide 106 forward into the reservoir 105 in the axial direction 118, fluid pressure increases, producing a reactionary force on the drive system 108 in the opposite direction which is transferred to the back plate 950. The capping member 112 prevents displacement of the sensor assembly 900 and effectively maintains the loading disc 960 and/or dowel member 928 in a fixed position with respect to the capping member 112 and/or housing 102. As a result, the reactionary force is transferred to the beams 902 by the loading disc 960 and/or rim portion 936 of the dowel member 928. In this manner, the capping member 112 is configured to deflect the beams 902 towards the surface 910 of the back plate 950 in response to the force provided by the drive system 108 in the axial direction 118. The deflection of the beams 902 is correlated with the axial force applied to the sensor assembly 900 and produces a corresponding increase in the strain exerted upon sensing elements 904. As set forth above, the control electronics 124 are electrically coupled to the sensing elements 904 and configured to determine the force provided or otherwise applied by the drive system 108 in the axial direction 118 based on electrical signals obtained from the sensing elements 904.

Referring now to FIGS. 3-6 and FIGS. 9-10, in accordance with one or more exemplary embodiments, the beam structure 370 of the sensor assembly 300 may include cantilevered arm portions 980 and dampening material 982 described above in the context of FIGS. 9-10. In such embodiments, when a compressive force applied to the sensor assembly 300 is within the intended measurement range, the cantilevered portions 980 and dampening material 982 negligibly influence displacement of the end portions 314 and/or deflection of the beams 302, and thus, do not influence force measurements obtained using sensing elements 304. In response to an impulse force applied to the sensor assembly, the cantilevered portions 980 and dampening material 982 dampen, retard, or otherwise impede additional displacement of the end portions 314 and/or deflection of the beams 302 towards the back plate 350, and thereby protect the sensing elements 304 and/or the beams 302 from potentially damaging deflection that may otherwise result from compressive impulse forces exceeding the intended measurement range.

Referring again to FIGS. 9-10, in accordance with one alternative embodiment, the thickness of the dampening material 982 may be chosen such that the dampening material 982 does not contact the surface 910 of the back plate 950 in response to compressive forces applied to the sensor assembly 900 that are within the intended measurement range for the sensor assembly 900. In such embodiments, any airgap separating the dampening material 982 from the surface 910 of the back plate 950 is less than the separation distance between the inner portion 918 and the surface 910 of the back plate 950, thereby allowing the dampening material 982 to contact the surface 910 of the back plate 950 before the inner portion 918 and/or end portions of the beams 902 contact the back plate 950. In this regard, when the force applied to the sensor assembly 900 meets or exceeds the upper end of the intended measurement range, the dampening material 982 dampens, retards, or otherwise impedes displacement of the end portions of the beams 902 (i.e., inner portion 918) towards the back plate 950, thereby reducing the rate of displacement of the inner portion 918 and/or end portions of the beams 902 before the inner portion 918 and/or end portions of the beams 902 contact the back plate 950. In other words, the cantilevered portions 980 and dampening material 982 slow the rate of deflection of the beams 902 before the end portions of the beams 902 contact the surface 910 of the back plate 950.

In accordance with another alternative embodiment, the cantilevered portions 980 may be substantially rigid and configured to contact the surface 910 of the back plate 950 to inhibit, prevent, or otherwise limit displacement of the inner portion 918 when the compressive force exceeds the intended measurement range for the sensor assembly 900. In such an embodiment, the separation distance between the cantilevered portions 980 and the surface 910 of the back plate 950 may be chosen such that the cantilevered portions 980 do not contact the surface 910 of the back plate 950 in response to compressive forces applied to the sensor assembly 900 that are within the intended measurement range for the sensor assembly 900. In such embodiments, any airgap separating the cantilevered portions 980 from the surface 910 of the back plate 950 is less than the separation distance between the inner portion 918 and the surface 910 of the back plate 950, such that the cantilevered portions 980 contact the surface 910 of the back plate 950 before the inner portion 918 and/or end portions of the beams 902 contact the back plate 950. As a result, in response to a compressive force applied to the sensor assembly 900 exceeding the intended measurement range, the rigid cantilevered portions 980 contact the back plate 950 to inhibit or otherwise prevent further displacement of the inner portion 918 with respect to the outer portion 906, thereby inhibiting or preventing additional deflection of the arm portions 912 of the beams 902, in a similar manner as described above in the context of FIGS. 3-6. It should be noted that in such alternative embodiments, the cantilevered portions 980 need not include the dampening material 982 to inhibit or prevent displacement of the inner portion 918.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the use of the sensor assembly 300 is not limited to the infusion pumps and drive systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A sensor assembly, comprising:
   a rigid structure;
   a beam comprising a supported portion affixed to the rigid structure and an end portion that is freestanding with respect to the rigid structure;
   a sensing element disposed on the beam; and
   a loading member to deflect the end portion of the beam towards the rigid structure in response to a force applied to the sensor assembly, the loading member having a feature that contacts the supported portion to prevent deflection of the beam when the force applied is greater than a threshold value.

2. The sensor assembly of claim 1, wherein the sensing element measures force applied to the sensor assembly that is less than the threshold value with a resolution less than or equal to 0.01 pounds.

3. The sensor assembly of claim 1, wherein the feature of the loading member comprises an extension portion that extends from an inner portion of the loading member.

4. The sensor assembly of claim 3, wherein the beam further comprises:
   an arm portion between the end portion and the supported portion.

5. The sensor assembly of claim 4, further comprising a dowel member coupling the loading member to the end portion.

6. The sensor assembly of claim 5, wherein the loading member comprises a planar portion, the dowel member separating the planar portion from the beam.

7. The sensor assembly of claim 4, wherein the sensing element comprises a strain gauge having a glass coating affixing the strain gauge to the arm portion.

8. The sensor assembly of claim 1, wherein the beam further comprises:
   an arm portion between the end portion and the supported portion, wherein the sensing element is disposed on the arm portion.

9. The sensor assembly of claim 8, wherein the loading member displaces the end portion with respect to the supported portion to deflect the arm portion when the force applied to the sensor assembly is less than the threshold value.

10. The sensor assembly of claim 2, wherein the threshold value is between 5.0 pounds and 10.0 pounds.

11. A portable medical device, comprising:
    a sliding member;
    a drive system to displace the sliding member in a first direction; and a sensor assembly coupled to the drive system to measure force provided by the drive system to displace the sliding member in the first direction, the sensor assembly comprising:
a rigid structure;
a beam comprising a supported portion affixed to the rigid structure and an end portion that is freestanding with respect to the rigid structure;
a sensing element disposed on the beam; and
a loading member arranged to deflect the end portion of the beam towards the rigid structure in response to a force applied to the sensor assembly, the loading member having a feature that contacts the supported portion to prevent deflection of the beam when the force applied to the sensor assembly is greater than a threshold value.

12. The portable medical device of claim 11, wherein the rigid structure comprises a back plate disposed between the beam and the drive system, and wherein the loading member deflects the beam towards the back plate in response to the force applied to the sensor assembly.

13. The portable medical device of claim 12,
wherein the loading member deflects the end portion towards the back plate in response to the force applied to the sensor assembly; and
the beam comprises an arm portion between the end portion and the supported portion, the sensing element being disposed on the arm portion.

14. The portable medical device of claim 13, wherein loading member contacts the supported portion to prevent displacement of the end portion with respect to the supported portion when the force applied to the sensor assembly is greater than the threshold value.

15. The portable medical device of claim 14, wherein loading member is a planar structure having a shoulder portion that contacts the supported portion when the force applied to the sensor assembly is greater than the threshold value.

16. The portable medical device of claim 12, further comprising a capping member in contact with the loading member to deflect the beam towards the back plate in response to the force provided by the drive system in the first direction.

17. The portable medical device of claim 11, wherein an electrical characteristic of the sensing element is influenced by deflection of the beam.

18. The portable medical device of claim 17, further comprising control electronics coupled to the sensing element to determine the force provided by the drive system to displace the sliding member in the first direction based on the electrical characteristic of the sensing element.

19. A sensor assembly, comprising:
a rigid structure;
a beam structure comprising a plurality of beams extending from an outer portion affixed to the rigid structure, each beam having a sensing element disposed thereon, wherein end portions of the beams are integral to provide an inner portion of the beam structure that is freestanding with respect to the rigid structure; and
a loading element mechanically coupled to the inner portion to deflect one or more of the plurality of beams by displacing the inner portion towards the rigid structure in response to a force applied to the loading element, the loading element contacting the outer portion to restrict displacement of the inner portion when the force applied is greater than a threshold value.

20. The sensor assembly of claim 19, wherein the loading element includes a shoulder portion to contact the outer portion of the beam structure when the force applied is greater than the threshold value.

21. The sensor assembly of claim 20, wherein the loading element includes a planar portion, the shoulder portion circumscribing the planar portion.

22. The sensor assembly of claim 21, further comprising a dowel member coupled to the loading element and the inner portion, wherein the dowel member has a rim portion between the inner portion and the loading element.

23. The sensor assembly of claim 22, wherein the rim portion separates the planar portion of the loading element from the beams.

* * * * *